United States Patent [19]

Weidenbach et al.

[11]  4,230,803

[45]  Oct. 28, 1980

[54] PREPARATION OF WATER-INSOLUBLE ENZYME COMPOSITIONS

[75] Inventors: Guenter Weidenbach, Hanover; Dirk Bonse, Arpke, both of Fed. Rep. of Germany

[73] Assignee: Kali-Chemie Aktiengesellschaft, Hanover, Fed. Rep. of Germany

[21] Appl. No.: 911,227

[22] Filed: May 31, 1978

[30] Foreign Application Priority Data

Jun. 10, 1977 [DE]  Fed. Rep. of Germany ....... 2726188

[51] Int. Cl.$^2$ ............................................... C07G 7/02
[52] U.S. Cl. .................................................. 435/176
[58] Field of Search ................... 195/63, 68, DIG. 4; 435/174; 11/176

[56] References Cited

U.S. PATENT DOCUMENTS

| | | | |
|---|---|---|---|
| 3,519,538 | 7/1970 | Messing et al. | 195/63 |
| 3,850,751 | 11/1974 | Messing | 195/63 |

OTHER PUBLICATIONS

Messing, R. A., Immobilized Enzymes for Industrial Reactors, Academic Press, N.Y. 1975, (pp. 71–78, 104, 108 and 109).

*Primary Examiner*—David M. Naff
*Attorney, Agent, or Firm*—Schwartz, Jeffery, Schwaab, Mack, Blumenthal & Koch

[57]  ABSTRACT

Enzymes are covalently bonded to porous inorganic supports by a process wherein maximum activity of enzyme in the water-insoluble enzyme composition is achieved with the lowest possible amount of enzyme. The process involves selecting an inorganic carrier having a most frequent pore-diameter that results in highest enzymatic activity possible per weight unit of the insoluble enzyme composition at the given enzyme concentration within the insoluble enzyme composition, and contacting the selected inorganic carrier with an enzyme solution containing an amount of enzyme which is sufficiently low so that the enzyme in the insoluble enzyme composition has a specific activity which is substantially the same as that of the enzyme in solution in the free state.

27 Claims, No Drawings

PREPARATION OF WATER-INSOLUBLE ENZYME COMPOSITIONS

BACKGROUND OF THE INVENTION

The present invention relates to a process for preparing a water-insoluble immobilized enzyme composition.

Methods for immobilizing enzymes are well known in the art. The terms "immobilizing enzymes" and "immobilized enzymes" as applied in the present specification mean that these enzymes are rendered essentially insoluble, so that they are rendered reusable and can be utilized in continuous processes. For this purpose enzymes are attached to insoluble support materials by means of adsorption or covalent bonding. Conventionally the support material is loaded with the enzyme by treating it with an enzyme solution.

Organic carrier materials (such as cellulose, nylon, or polyacrylamide) exhibit serious disadvantages since they do not possess sufficient mechanical strength, can be affected by the action of solvents, and are sensitive to changes in the pH-value or the ion concentration in the surrounding medium. Furthermore, several of these organic materials are susceptible to being attacked by microbes which may cause a loosening of the bond between the enzyme and the support material.

Therefore, inorganic materials have been suggested as carrier materials onto which enzymes may be attached by means of adsorption or covalent bonding. Which type of attachment is preferred depends on the properties of the substrate for which, and on the conditions under which the enzyme is to be utilized. If the substrate is in a medium which contains a high salt concentration, an attachment by mere adsorption cannot be used, since desorption of the adsorbed enzyme molecules may occur. Therefore, a covalent bonding between the enzyme and the carrier is preferred. For this, the carrier surface must include a sufficient amount of functional groups which are capable of forming a covalent bond with the respective enzyme. Since most inorganic carrier materials do not contain such specific functional groups, a pretreatment of the carrier surface is necessary. A conventional method for providing functional organic groups in the surface of an inorganic carrier material comprises loading the inorganic materials with silanes, which attach to the surface of the carrier material and provide the latter with functional organic groups, preferably alkylamino groups, which are capable of forming a covalent bond with organic compounds. Treatment of the inorganic carrier material with glutardialdehyde, sulfuryl chloride, thionyl chloride, or cyanur chloride, has also been tried.

It also is possible to provide the surface of the inorganic carrier material with a coating of a water-insoluble organic polymer which comprises free functional groups, for example, a polyacrolein which comprises between about 10 and about 70% of free aldehyde groups relative to the number of monomer units.

Aluminum oxides, nickel oxide, iron oxide, titanium oxide, zirconium oxide, hydroxyapatite, silicates, and porous glass have been proposed as porous inorganic carrier materials. The pore-structure within these carrier materials has to be such that the enzyme is able to reach the inner surface of the support particles. Yet, with regard to which additional properties of the carrier material are desirable, i.e., which are the optimum pore-size distributions and/or surface areas, the available information differs largely from each other.

Independently of the type of bonding between enzyme and support material, and the use of any of the aforementioned support materials, it has not yet been possible to immobilize enzymes in such a manner that the specific activity of the enzyme in the immobilized state reaches the value of the specific activity of the enzyme in the free state. According to D. L. Latigue (see Immobilized Enzymes for Industrial Reactors, London, 1975, p. 127), even under the most favorable immobilizing conditions only 80% at the most of the enzyme which is attached to the support material is present in active form.

SUMMARY OF THE INVENTION

It is an object of the present invention to provide a process for preparing an immobilized enzyme composition wherein the enzyme is covalently bonded to an inorganic support material, whereby a maximum activity of the immobilized enzyme composition is achieved by using the lowest possible amount of enzyme.

It is a further object of the present invention to provide such a process by which an immobilized enzyme composition is obtained which exhibits the highest enzymatic activity per weight unit of the composition which is possible at the given enzyme concentration within the composition.

It is a further object of the present invention to provide such a process by which a high specific activity of the enzyme in the immobilized state within the composition is achieved, in particular a specific activity of the enzyme in the immobilized state, which is in the same order as that of the enzyme in the free state.

It is a further object of the present invention to provide such a process by which immobilized enzyme compositions for industrial reactors can be prepared at relatively low costs.

It is a further object of the present invention to provide a process for determining the pore-structure of a carrier material and the concentration of an enzyme composition which are most favorable for preparing an immobilized enzyme composition wherein the enzymatic activity per weight unit of the composition and the specific activity of the immobilized enzyme therein are high.

In order to accomplish the foregoing objects according to the present invention, there is provided an improved process for preparing a water-insoluble enzyme composition having a high enzymatic activity and containing the enzyme covalently bonded to an inorganic support material comprising the steps of (a) contacting an inorganic support material which is capable of covalently binding the enzyme with a solution of the enzyme in an aqueous solvent, whereby a portion of the enzyme is taken up by the support material and covalently bonded thereto, to form a water-insoluble enzyme-containing composition, and (b) separating the water-insoluble enzyme-containing composition from the remaining solution, wherein the improvement comprises the inorganic support material, having a pore-size distribution wherein the most frequent pore-diameter is such that in the resulting enzyme composition for any enzyme concentration contained therein, the enzymatic activity per weight unit of the composition is the highest activity per weight unit of the composition which is obtainable at this enzyme concentration, and the enzyme solution comprising such an amount of enzyme which is sufficiently low that the enzyme which is bonded in the resulting enzyme composition has a specific activity which substantially is about the same as that of the enzyme in the free state.

Further objects, features, and advantages of the present invention will become apparent from the detailed description of the invention and its preferred embodiments which follows.

DETAILED DESCRIPTION OF THE INVENTION AND ITS PREFERRED EMBODIMENTS

Conventional inorganic carrier materials can be utilized within the process according to the present invention. Such carrier materials comprise hydroxy-group-containing oxides of elements selected from the group consisting of silicon, aluminum, nickel, iron, titanium, zirconium, or mixtures thereof.

In order to obtain a support material which is capable of covalently binding the enzyme, it is preferred to provide, in a conventional manner, the inorganic material with a coupling agent which is sufficiently strongly attached to the carrier material preferably by means of a covalent bond and also is capable of forming a covalent bond with the enzyme. As mentioned above, various different coupling agents are known in the art and any of these conventional coupling agents can be utilized within the present invention.

Until now organic silanes have been most commonly used and methods for silanizing the inorganic carrier material are well known in the art. Preferably, the inorganic carrier material is treated with a solution of the silane in a high-boiling solvent, e.g., a high-boiling aromatic or aliphatic hydrocarbon, in particular benzene or toluene.

The amount of coupling agent must be suitably high to provide a sufficient number of functional groups on the carrier surface and will depend largely on the surface area of the carrier material which is used.

Suitable silane coupling agents comprise silanes, having the formula

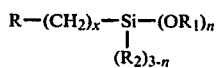

wherein $R_1$ and $R_2$ each represent lower alkyl, preferably methyl, n represents 1–3, x represents 1–5, preferably 3 and R represents a functional group which is capable of forming a covalent bond with the enzyme, e.g., amino or carbonyl.

Other suitable organic coupling agents comprise lower dialdehydes such as glutardialdehyde.

According to the present invention, the most favorable most frequent pore-diameter of an inorganic support material which is to be used as starting material for preparing a specific enzyme/support composition and the most favorable amount of the enzyme which is to be included into the starting enzyme solution are determined as follows:

Different inorganic carrier materials of the same chemical composition yet which are distinguished from each other by a different most frequent pore-diameter are pretreated with a coupling agent to obtain the support material which is capable of covalently binding the enzyme. Then, various amounts of the enzyme are offered to each of the pretreated support materials by contacting them with various solutions of the enzyme, each having a different enzyme content and attaching the enzyme to the support material in a conventional manner by forming a covalent bond between the enzyme and the functional group of the coupling agent. The enzymatic activity per weight unit of the thus obtained compositions is determined. The results indicate that regardless of the amount of enzyme which is bonded in the composition, the activity of the composition is always dependent on the most frequent pore-diameter, and passes through a maximum at a certain pore-diameter range. Furthermore, it has been found that the particle-size of the support material is substantially irrelevant with regard to the pore-diameter range at which the maximum occurs and at the most, might influence the actual value of the maximum. Therefore, the particle-size of the immobilized enzyme composition is only of minor significance within the context of the present invention and can be chosen mainly depending on the intended use of the composition, e.g., the viscosity of the substrate for which, and the reaction conditions under which it is to be used.

The inorganic support material is selected which has the most favorable most frequent pore-diameter which, independently of the enzyme contents in the enzyme solutions, yields the enzyme composition having the highest enzymatic activity per weight unit among the group of enzyme compositions obtained from the same enzyme solutions.

Again, various amounts of the enzyme are offered to this inorganic support material having the most favorable most frequent pore-diameter by contacting it with solutions containing different amounts of the enzyme. The specific activity of the enzyme which is bonded in the resulting enzyme compositions is determined and is compared with that of the enzyme in free state. From the results, it is apparent that at a certain enzyme concentration, enzyme compositions are obtained wherein the specific activity of the enzyme in the bond state nearly or completely reaches that of the enzyme in the free state, that is the relative activity of the composition reaches 100%.

According to a preferred embodiment of the present invention, the inorganic carrier material comprises a $SiO_2$-gel. Preferably, the $SiO_2$-gel is obtained by adjusting the alkali-content expressed as % by weight of $Na_2O$ to from about 0.1 to about 0.5% by weight, drying the gel, and calcining the gel at a temperature of from about 400° to about 850° C., preferably from about 570° to about 750° C., in a flow of water-vapor-containing air during a period of from about 5 to about 10 hours.

It is advisable to carry out the drying at a temperature of between about 180° and about 200° C. under water-vapor-saturated air. The calcining is advantageously effected under a flow of air having a relative humidity of between about 40 and about 80%.

The pore-size distribution in the resulting carrier material is such that the most frequent pore-diameter is in the range of between about 175 and about 3,000 Å, preferably in the range of between about 250 and about 600 Å, most preferably about 340 Å.

The process for immobilizing enzymes according to the present invention can be applied to any enzymes, e.g., any enzymes which are utilized for technical or analytical purposes, for example, hydrolytic enzymes such as amylases, glucosidases, or proteases, redox enzymes such as glucose-oxidase or catalase, isomerases such as glucose-isomerase, or transferase enzymes such as dextran-sucrose-transferase.

According to an especially preferred embodiment of the invention, the enzyme is amyloglucosidase which in the free state exhibits a specific activity of from about 10 to about 15 units/mg, and the support material comprises the $SiO_2$-gel support material according to the above defined preferred embodiment. Most preferably the most frequent pore-diameter of this support material is between about 250 and about 600 Å, in particular between about 300 and about 400 Å, especially about 340 Å. The most favorable immobilized amyloglucosidase composition is obtained if this support material is contacted with a solution containing from about 25 to about 75, preferably about 50 mg of amyloglucosidase per 1 g of support material.

Any conventional coupling agent may be used in this composition, for example a silane of the above mentioned formula or glutardialdehyde.

According to another especially preferred embodiment of the present invention, the enzyme is glucose-isomerase which in the free state exhibits a specific activity of from about 50 to about 70 units/mg, and the support material comprises the $SiO_2$-gel support material according to the above defined preferred embodiment. Most preferably the most frequent pore-diameter of this support material is between about 250 and about 600 Å, in particular between about 300 and about 400 Å, especially about 340 Å. The most favorable immobilized glucose-isomerase composition is obtained if this support material is contacted with a solution containing from about 20 to about 50, preferably about 25 mg of glucose-isomerase per 1 g of support material.

Any conventional coupling agent may be used in this composition, for example, a silane of the above mentioned formula or glutardialdehyde.

The invention will now be further illustrated by the following examples which are intended to be illustrative only.

EXAMPLE 1

1.0 Preparation of support material No. 1.0.

$SiO_2$-gel, having an alkali-content of 0.3% by weight of $Na_2O$, which has been precipitated from a sodium-silicate solution by means of sulfuric acid, is dried for a period of 3 hours at a temperature of 180° C. in an atmosphere of water-vapor-saturated air. 1 kg of this material is calcined at a temperature of 730° C. for a period of 6 hours in a stream of air, the relative humidity of which is 80% and the flow-rate of which is 2 l/min. In the $SiO_2$ resulting from this treatment the pore-size distribution is characterized by a most frequent pore-diameter of about 1400 Å. The carrier material is divided into various particle-size fractions by passing it through various sieves of different mesh size. The fraction, having a particle-size of from about 0.25 to about 0.5 mm, is used for preparing the support material.

A mixture of 150 g of this carrier material fraction and 4 l of a 10% solution of γ-aminopropyltriethoxy silane in benzene is heated to reflux temperature for a period of 8 hours. Then the reaction mixture is cooled and the resulting support material is filtered off and washed 3 times with 1000 ml of benzene each and 3 times with 1000 ml of acetone each. After evaporating the solvent under vacuum at room temperature, the support material is washed twice with a 0.05 m phosphate buffer solution (pH 7), 3 times with bidistilled water, and then is dried over $P_2O_5$ under vacuum. From the average C- and N-content which are determined by elemental analysis, the silane-content of the support is calculated. According to this calculation, the support No. 1.0 contains 0.13 m equivalents of silane/g.

1.1 Preparation of immobilized enzyme composition No. 1.1.

10 g of this support material No. 1.0 are suspended in 20 ml of a solution of 1 g of amyloglucosidase (Commercial Product Merck 1330) in a 0.05 m phosphate buffer solution (pH 7). The degree of activity of the amyloglucosidase is 11.75 unit/mg, whereby 1 activity unit is equivalent to the formation of 1 μmole of glucose/min. at a temperature of 25° C. This suspension is kept under vacuum for a period of 20 minutes then air is allowed to reenter, and after a period of 2 hours the vacuum is re-applied for a period of 20 minutes. After a period of 4 hours, the support material is separated from the solution by means of filtration, subsequently is washed 3 times with bidistilled water and finally washed 3 times with a 0.01 m phosphate buffer solution (pH 5). The resulting final composition 1.1 is stored in a phosphate buffer solution (pH 5) at a temperature of 4° C. The C- + N-content which is determined by means of elemental analysis, shows a protein content of 16.5 mg/g.

1.2 Preparation of immobilized enzyme composition No. 1.2.

10 g of the silanized support material No. 1.0 is suspended in 20 ml of a solution of 0.5 g of amyloglucosidase (Commercial Product Merck 1330) in 0.05 m phosphate buffer solution (pH 7). The suspension is further treated as described under 1.1. The C- and N-content of the resulting composition 1.2 indicates a protein content of 9.0 mg/g.

EXAMPLE 2

2.0 Preparation of support material No. 2.0.

A $SiO_2$-gel, having a $Na_2O$-content of 0.3% by weight, which has been precipitated from a sodium-silicate solution by means of sulfuric acid, is dried as described in Example 1. 1 kg of this material is calcined for a period of 6 hours at a temperature of 680° C. in a stream of air, having a relative humidity of 80% and a flow-rate of 2 l/min. After this treatment the pore-size distribution of the $SiO_2$ is characterized by a most frequent pore-diameter of 340 Å. The carrier material No. 2.0 is separated into different particle-size fractions by passing it through sieves of appropriate mesh size. The fraction, having a particle-size of 0.25 to 0.5 mm, is used for preparing the support material No. 2.0.

150 g of this fraction of the carrier material is treated with 4 l of a 10% solution of γ-aminopropyltriethoxy silane in benzene as is described in Example 1, for a period of 8 hours.

The silane content of the support material No. 2.0 is 0.19 m equivalents of silane/g, as calculated from the average C- and N-content which is determined by elemental analysis.

2.1 Preparation of immobilized enzyme composition No. 2.1.

10 g of the support material No. 2.0 are suspended in 20 ml of a solution of 1 g of amyloglucosidase (Commercial Product Merck 1330) in a 0.05 m phosphate buffer solution (pH 7). This suspension is further treated as described in Example 1. The C- and N-content of the resulting composition 2.1 shows a protein content of 30.8 mg/g.

2.2 Preparation of immobilized enzyme composition No. 2.2.

10 g of the silanized support material No. 2.0 are suspended in 20 ml of a solution of 0.5 g of amyloglucosidase (Commercial Product Merck 1330) in a 0.05 m phosphate buffer solution (pH 7). This suspension is further treated as described in Example 1 for the preparation of the composition No. 1.2. The C- and N-content of the resulting composition No. 2.2 shows a protein content of 17.4 mg/g.

EXAMPLE 3

3.0 Preparation of support material No. 3.0.

A $SiO_2$-gel, having a $Na_2O$-content of 0.3% by weight, which has been precipitated from a sodium silicate solution by means of sulfuric acid, is dried as described in Example 1. 1 kg of this material is calcined for a period of 6 hours at a temperature of 640° C. in a stream of air having a relative humidity of 60% and a flow-rate of 2 l/min. After this treatment, the particle-size distribution of the $SiO_2$ is characterized by a most frequent pore-diameter of 180 Å. The carrier material No. 3.0 is separated into various particle-size fractions by passing it through sieves of appropriate mesh size. The fraction, having a particle-size of 0.25 to 0.50 mm, is used for preparing the support material No. 3.0.

150 g of this fraction of carrier material No. 3.0 is treated for a period of 8 hours with 4 l of a 10% solution of γ-aminopropyltriethoxy silane in benzene as described in Example 1. The silane-content of the resulting support material No. 3.0 is 0.51 m equivalents of silane/g as calculated from the average C- and N-content which is determined by elemental analysis.

3.1 Preparation of immobilized enzyme composition No. 3.1.

10 g of this support material No. 3.0 are suspended in 20 ml of a solution of 1 g of amyloglucosidase (Commercial Product Merck 1330) in a 0.05 m phosphate buffer solution (pH 7). The suspension is further treated as described in Example 1. The C- and N-content of the resulting composition 3.1 indicates a protein-content of 26.2 mg/g.

3.2 Preparation of immobilized enzyme composition No. 3.2.

Another 10 g of the silanized support material No. 3.0 are suspended in 20 ml of a solution of 0.5 g of amyloglucosidase (Commercial Product Merck 1330) in a 0.05 m phosphate buffer solution (pH 7). This suspension is treated as described in Example 1. The C- and N-content of the final composition No. 3.2, indicates a protein-content of 12.7 mg/g.

EXAMPLE 4

4.0 In order to demonstrate, that the activity of the immobilized enzyme composition is not influenced by the type of coupling agent in the support material, support material No. 4.0 is prepared as follows:

By passing the carrier material No. 2.0 (most frequent pore-diameter 340 Å) through sieves of appropriate mesh size, the carrier material fraction having a particle-size of 0.25 to 0.5 mm, is obtained. 50 g of this fraction are suspended in 500 ml of a 12.5% aqueous solution of glutardialdehyde and this suspension is stirred for a period of 5 minutes at room temperature. Subsequently 500 ml of a saturated $NH_4Cl$-solution are added. The mixture is agitated at room temperature for a period of 4 hours, then the support material No. 4.0 is filtered off and washed with water until it is void of chloride ions, and then is dried under vacuum over $P_2O_5$.

4.1 Preparation of immobilized enzyme composition No. 4.1.

10 g of the support material No. 4.0 are suspended in 20 ml of a solution of 1 g of amyloglucosidase (Commercial Product Merck 1330) in a 0.05 m phosphate buffer solution (pH 7). This suspension is further treated as described in Example 1. The C- and N-content of the final composition indicates a protein-content of 29.8 mg/g.

4.2 Preparation of immobilized enzyme composition No. 4.2.

Another 10 g of the support material No. 4.0 are suspended in 20 ml of a solution of 0.5 g of amyloglucosidase (Commercial Product Merck 1330) in a 0.05 m phosphate buffer solution (pH 7). This suspension is treated as described for composition 1.2 in Example 1. The C- and N-content of the resulting composition 4.2 indicates a protein-content of 17.9 mg.

EXAMPLE 5

5.1 Preparation of immobilized enzyme composition No. 5.1.

10 g of the support material No. 1.0 (most frequent pore-diameter 1400 Å) are suspended in 40 ml of a 0.05 m phosphate buffer solution (pH 7), which contains 0.5 g of glucose-isomerase (Y. Takasaki, Agr. Biol. Chem. 33, No. 11, pp. 1527–1534 (1969)). The mixture is allowed to react at room temperature for a period of 30 minutes. After periods of 10 minutes each, the reaction-flask is evacuated, and after the reaction is completed, the remaining solution is filtered off with suction. Subsequently, the composition is washed 3 times with water and with 0.05 m phosphate buffer solution (pH 7). The C- and N-content of the resulting composition 5.1 indicates a protein-content of 4.8 mg/g.

5.2 Preparation of immobilized enzyme composition No. 5.2.

10 g of the support material No. 1.0 are suspended in 40 ml of a 0.05 m phosphate buffer solution (pH 7), which contains 0.25 g of glucose-isomerase. This suspension is further treated as described under 5.1. The C- and N-content of the resulting composition 5.0 indicates a protein-content of 2.0 mg/g.

EXAMPLE 6

6.1 Preparation of immobilized enzyme composition No. 6.1.

10 g of the support material No. 2.0 (most frequent pore-diameter 340 Å) are suspended in 40 ml of a 0.05 m phosphate buffer solution (pH 7), which contains 0.5 g of glucose-isomerase. This suspension is further treated as described in Example 5. The C- and N-content of the resulting composition No. 6.1 indicates a protein-content of 22.0 mg/g.

6.2 Preparation of immobilized enzyme composition No. 6.2.

10 g of the support material No. 2.0 are suspended in 40 ml of a 0.05 m phosphate buffer solution (pH 7), which contains 0.25 g of glucose-isomerase. This suspension is further treated as described in Example 5. The C- and N-content of the resulting composition No. 6.2 indicates a protein-content of 10.2 mg/g.

EXAMPLE 7

7.1 Preparation of immobilized enzyme composition No. 7.1.

10 g of the support material No. 3.0 (most frequent pore-diameter 180 Å) are suspended in 40 ml of a 0.05 m phosphate buffer solution (pH 7), which contains 0.5 g of glucose-isomerase. This suspension is further treated as described in Example 5. The C- and N-content of the resulting composition 7.1 indicates a protein-content of 11.2 mg/g.

7.2 Preparation of immobilized enzyme composition No. 7.2.

10 g of the support material No. 3.0 are suspended in 40 ml of a 0.05 m phosphate buffer solution (pH 7), which contains 0.25 g of glucose-isomerase. This suspension is further treated as described in Example 5. The C- and N-content of the resulting composition 7.2 indicates a protein-content of 5.1 mg/g.

EXAMPLE 8

8.1 Preparation of immobilized enzyme composition No. 8.1.

10 g of support material No. 4.0, which is prepared as described in Example 4 (most frequent pore-diameter 340 Å, carrier material treated with an aqueous solution of glutardialdehyde) are suspended in 40 ml of a 0.05 m phosphate buffer solution (pH 7), which contains 0.5 g of glucose-isomerase. This suspension is further treated as described in Example 5. The C- and N-content of the resulting composition 8.1 indicates a protein-content of 21.3 mg/g.

8.2 Preparation of immobilized enzyme composition No. 8.2.

10 g of the same support material No. 4.0 are suspended in 40 ml of a 0.05 m phosphate buffer solution (pH 7), which contains 0.25 g of glucose-isomerase. This suspension is further treated as described in Example 5. The C- and N-content of the resulting composition 8.2 indicates a protein-content of 9.8 mg/g.

EXAMPLE 9

The activity of the immobilized enzyme composition No. 1.1, 1.2, 2.1, 2.2, 3.1, 3.2, 4.1, and 4.2 and the activity of the enzyme which is used in these compositions (amyloglucosidase, Commercial Product Merck 1330) is determined by reaction with dinitrosalicylic acid according to the method described by W. Rick and H. P. Stegbauer, in H. U. Bergmeyer, "Methoden der Enzymatischen Analyse", Verlag Chemie 1970, p. 848. One activity-unit (U) is equivalent to such an amount of enzyme which liberates 1μ equivalents of reducing groups (calculated as glucose) per minute under the incubation conditions described below.

Incubation conditions

Substrate: A 2% solution of starch (Commercial Product Zulkowsky-Staerke Merck 1257) in an 0.1 m acetate buffer solution, the pH of which is 5.0; incubation period: 30 minutes; incubation temperature 25° C.

In a 40 ml reactor, the immobilized enzyme compositions are suspended under the aforementioned conditions and under agitation at an agitation rate of 600 turns/min.

The protein content is calculated from the average C- and N-content which is determined by means of elemental analysis. The most frequent pore-diameter is determined from the pore-size distribution which is determined in a high-pressure porosimeter. The characteristics of the compositions, which are described in Examples 1 to 4, are summarized in Table I below. The following definitions are used:

| | | |
|---|---|---|
| Most frequent pore-diameter | D | (Å) |
| Enzyme content | $c_E$ | (mg enzyme/g of support) |
| Activity absolute | U | (units/g of composition) |
| Spec. activity of the enzyme in the immobilized state | $U_s =$ | $U/c_E$ (units/mg of enzyme) |
| Spec. activity of the enzyme in the free state | $U_{SF}$ | (units/mg enzyme) |
| Relative | $U_{rel} =$ | $100 \cdot \frac{U_s}{U_{SF}}$ (%) |

TABLE I

Immobilized Amyloglucosidase Composition

| Sample of Composition No. | Most frequent pore-diameter D | Enzyme-Content $c_E$ | U | $U_s$ | $U_{rel}$ | $U_{SF}$ |
|---|---|---|---|---|---|---|
| 1.1 | 1400 | 16.5 | 98.4 | 5.96 | 51 | 11.75 |
| 1.2 | | 9.0 | 100.5 | 11.16 | 95 | |
| 2.1 | 340 | 30.8 | 208.8 | 6.77 | 58 | |
| 2.2 | | 17.4 | 203.9 | 11.71 | 100 | |
| 3.1 | 180 | 26.2 | 150.0 | 5.72 | 49 | |
| 3.2 | | 12.7 | 149.5 | 11.77 | 100 | |
| 4.1 | 340 | 29.8 | 199.7 | 6.70 | 57 | |
| 4.2 | | 17.9 | 209.4 | 11.70 | 100 | |

EXAMPLE 10

The activity of the composition No. 5.1, 5.2, 6.1, 6.2, 7.1, 7.2, 8.1, and 8.2, which are described in Examples 5 to 8, and the activity of the glucose-isomerase which is used in these compositions, is determined according to the method described by Takasaki (see Y. Takasaki: Agr. Biol. Chem. Col. 30, No. 12, pp. 1247-1253, (1966), and Z. Dische and E. Borenfreund: J. Biol. Chem. 192, 583, (1951)). One activity-unit corresponds to such an amount of enzymes, by which 1 mg of fructose is formed under the incubation conditions described below.

Incubation conditions

Temperature—65° C.

Reaction-period—1 h

Substrate—0.1 m glucose $\times H_2O$ (Merck 8342) in 0.05 m phosphate buffer, pH 8.0 containing 0.0004 m $MgSO_4$.

The immobilized glucose-isomerase compositions are suspended in a stirring-reactor under the same conditions as described in Example 9.

The protein-content of the compositions is calculated from the average C- and N-content which is determined by means of elemental analysis.

In Table II below the properties of the compositions described in Examples 5 to 8, are summarized.

The same definitions as in Example 9 are used.

TABLE II

| Sample of Composition No. | Immobilized glucose-isomerase compositions | | ACTIVITY | | | |
|---|---|---|---|---|---|---|
| | Most frequent pore-diameter D | Enzyme-Content $c_E$ | U | $U_s$ | $U_{rel}$ | $U_{SF}$ |
| 5.1 | 1400 | 4.8 | 115.4 | 24.0 | 41 | 58.9 |
| 5.2 | | 2.0 | 117.3 | 58.7 | 99 | |
| 6.1 | 340 | 22.0 | 558.5 | 25.4 | 43 | |
| 6.2 | | 10.2 | 556.1 | 54.5 | 93 | |
| 7.1 | 180 | 11.2 | 291.0 | 26.0 | 44 | |
| 7.2 | | 5.1 | 292.3 | 57.3 | 97 | |
| 8.1 | 340 | 21.3 | 543.2 | 25.5 | 43 | |
| 8.2 | | 9.8 | 544.0 | 55.5 | 94 | |

From the foregoing data it is apparent that:

1. The activity U of the examined compositions passes through a maximum which is dependent on the most frequent pore-diameter of the support material.

2. The specific activity $U_s$ is dependent on the enzyme content and, at a certain enzyme-concentration, the specific activity $U_s$ of the immobilized enzyme reaches about the same value as the specific activity $U_{SF}$ of the enzyme in the free state, that is, $U_{rel}$ reaches about 100. If this enzyme-concentration is exceeded, the specific activity is reduced, whereby the value of the product $U_s \times c_E$ remains constant.

3. The amount of enzyme which is taken up by the support material is a function of the most frequent pore-diameter.

The system enzyme/support exhibits a maximum activity at a lowest possible enzyme-content, if the best suited carrier 2.0 (most frequent pore-diameter 340 Å) has taken up 17.4 mg of amyloglucosidase/g or 10.2 mg of glucose-isomerase/g (compositions No. 2.2 and 6.2).

4. The enzyme-uptake and the activity of the examined compositions, are independent of the utilized coupling agent.

The costs for enzymes are very high and increase considerably if an increased degree of purity is required. Accordingly, these costs are an important factor in determining the technical possibilities for the industrial use of enzymes.

What is claimed is:

1. A process for preparing a water-insoluble enzyme composition wherein an enzyme is covalently bonded to an inorganic support material whereby a maximum activity of the insoluble enzyme composition is achieved with the lowest possible amount of enzyme, said process comprising the steps of:
   (a) selecting an inorganic support material having the most frequent pore-diameter which produces an enzyme composition having the highest absolute activity when a plurality of inorganic support materials having different most frequent pore-diameters are each individually contacted with an enzyme solution containing a given concentration of enzyme, said most frequent pore-diameter producing the highest absolute activity being independent of the enzyme concentration in the solution;
   (b) selecting an aqueous enzyme solution containing the concentration of enzyme which produces a composition that has a relative activity of substantially 100% when the support material of step (a) is contacted with a plurality of enzyme solutions having different concentrations of enzyme;
   (c) contacting the support material of step (a) with the enzyme solution of step (b) whereby a portion of the enzyme from the solution is taken up by the support material to produce a water-insoluble enzyme composition; and
   (d) separating the resulting water-insoluble enzyme composition from the remaining solution.

2. The process as defined in claim 1 which further comprises the step of bonding a coupling agent to an inorganic carrier material to obtain an inorganic support material which is capable of covalently bonding the enzyme.

3. The process as defined in claim 2, wherein the inorganic carrier material comprises a hydroxy-group-containing oxide of at least one element selected from the group consisting of silicon, aluminum, nickel, iron, titanium, zirconium, or mixtures thereof.

4. The process as defined in claim 2, wherein the inorganic support material which is capable of covalently bonding the enzyme is a silanized silicon oxide gel.

5. The process as defined in claim 1, wherein the inorganic support material comprises a silicon dioxide-gel.

6. The process as defined in claim 5 which further comprises the step of preparing a silicon dioxide-gel by adjusting the alkali content expressed as % by weight of $Na_2O$ to from about 0.1 to about 0.5% by weight, drying the gel, and calcining the dried gel at a temperature of from about 400° to about 850° C. in a flow of water-vapor-containing air during a period of from about 5 to about 10 hours.

7. The process as defined in claim 6, wherein the calcining temperature is from about 570° to about 750° C.

8. The process as defined in claim 6, wherein the drying is effected at a temperature of between about 180° C. and about 200° C. under water-vapor-saturated air.

9. The process as defined in claim 6, wherein the calcining is effected in a flow of air having a relative humidity of between about 40 and about 80%.

10. The process as defined in claim 1, wherein the enzyme is selected from the group consisting of hydrolytic enzymes, redox enzymes, isomerases, and transferase enzymes.

11. The process as defined in claim 10, wherein the hydrolytic enzymes are selected from the group consisting of amylases, glycosidases, and proteases.

12. The process as defined in claim 11, wherein the enzyme is amyloglucosidase.

13. The process as defined in claim 11, wherein the enzyme solution contains from about 25 to about 75 mg of amyloglucosidase per 1 g of support material.

14. The process as defined in claim 13, wherein the amount of amyloglucosidase is about 50 mg per 1 g of support material.

15. The process as defined in claim 13, wherein the amyloglucosidase exhibits a specific activity in the free state of from about 10 to about 15 units/mg.

16. The process as defined in claim 13, wherein the support material comprises a silicon dioxide-gel having a most frequent pore-diameter of from about 300 to about 400 Å.

17. The process as defined in claim 10, wherein the enzyme is glucose-isomerase.

18. The process as defined in claim 17, wherein the enzyme solution contains from about 20 to about 50 mg of glucose-isomerase per 1 g of support material.

19. The process as defined in claim 18, wherein the amount of glucose-isomerase is about 25 mg per 1 g of support material.

20. The process as defined in claim 18, wherein the glucose-isomerase exhibits a specific activity in the free state of from about 50 to from about 70 units/mg.

21. The process as defined in claim 18, wherein the support material comprises a silicon dioxide-gel having a most frequent pore-diameter of from about 300 to about 400 Å.

22. The process as defined in claim 2, wherein the inorganic support material which is capable of covalently bonding the enzyme is a silicon oxide gel, which is treated with glutardialdehyde.

23. A process according to claim 1, wherein the inorganic support material is selected by:
(a1) contacting a plurality of individual inorganic support materials having different most frequent pore-diameters with at least one enzyme solution to produce insolubilized enzyme compositions;
(a2) measuring the absolute activity of each of the resulting insolubilized enzyme compositions;
(a3) comparing the measured values for the different support materials; and
(a4) selecting the support material having the most frequent pore-diameter which produces the enzyme composition having the highest absolute activity.

24. A process according to claim 1, wherein the enzyme solution is selected by:
(b1) contacting the support material of step (a) with a plurality of enzyme solutions containing different concentrations of enzyme to produce insolubilized enzyme compositions;
(b2) measuring the amount of enzyme taken up by each of the support materials and determining the specific activity of each of the insolubilized enzyme compositions;
(b3) determining the relative activity of the enzyme in each of the enzyme compositions from the specific activity of the insolubilized enzyme compositions and the specific activity of the enzyme in the free state in the enzyme solutions; and
(b4) determining the enzyme solution which produces an insolubilized enzyme composition having a relative activity of substantially 100%.

25. Process according to claim 1, wherein the water-insoluble enzyme composition from step d) has the highest enzyme activity per weight unit of the composition which is obtainable at the concentration of enzyme contained in said composition.

26. Process according to claim 24, wherein the enzyme solution of step (b4) produces an insolubilized enzyme composition having the highest activity per weight unit of composition which is obtainable at that enzyme concentration.

27. A process of producing a water-insoluble enzyme composition wherein an enzyme is covalently bonded to an inorganic support material whereby maximum activity of the insoluble enzyme composition is achieved with the lowest possible amount of enzyme comprising the steps of:
(a') contacting at least 2 different inorganic support materials capable of covalently bonding the enzyme, each having a different most frequent pore-diameter, each with at least two different solutions of the enzyme, each having a different enzyme content to form a water-insoluble enzyme composition;
(b') determining the enzymatic activity per weight unit of the enzyme compositions obtained in step (a');
(c') comparing enzymatic activities of the enzyme compositions determined in step (b') and determining the inorganic support material having the most frequent pore-diameter that yields the enzyme composition having the highest enzymatic activity for the at least two different solutions of enzyme;
(d') contacting the inorganic support material having the most frequent pore-diameter determined in step (c') with a plurality of solutions containing different amounts of the enzyme to form a plurality of water-insoluble enzyme compositions;
(e') determining the specific activity of each of the plurality of enzyme compositions obtained in step (d');
(f') comparing the specific activity of each water-insoluble enzyme composition determined in step (e') with the specific activity of the enzyme in the free state contained in each of said plurality of enzyme solutions to determine the relative activity of each water-insoluble enzyme composition;
(g') determining from the different amounts of enzyme in the enzyme solutions the amount which yields a water-insoluble enzyme composition having a relative activity of substantially 100%;
(h') contacting the inorganic support material having the most frequent pore-diameter as determined in step (c') with a solution containing the amount of enzyme as determined in step (g') to form a water-insoluble enzyme composition; and
(i') separating the water-insoluble enzyme composition from the remaining solution.

* * * * *